United States Patent
Housley

(10) Patent No.: US 8,779,918 B2
(45) Date of Patent: Jul. 15, 2014

(54) CONVULSIVE SEIZURE DETECTION AND NOTIFICATION SYSTEM

(76) Inventor: Richard Housley, Plympton, MA (US)

( * ) Notice: Subject to any disclaimer, the term of this patent is extended or adjusted under 35 U.S.C. 154(b) by 44 days.

(21) Appl. No.: 13/328,233

(22) Filed: Dec. 16, 2011

(65) Prior Publication Data
US 2013/0154827 A1 Jun. 20, 2013

(51) Int. Cl.
*G08B 1/08* (2006.01)
(52) U.S. Cl.
USPC ...................... 340/539.12; 600/595
(58) Field of Classification Search
CPC ............................ A61B 5/0488; A61B 5/4538
USPC ............. 340/539.12; 600/324, 544, 546, 595
See application file for complete search history.

(56) References Cited

U.S. PATENT DOCUMENTS

| 8,075,499 | B2 * | 12/2011 | Nathan et al. | 600/595 |
| 2012/0053491 | A1 * | 3/2012 | Nathan et al. | 600/595 |
| 2012/0108999 | A1 * | 5/2012 | Leininger et al. | 600/546 |
| 2012/0190949 | A1 * | 7/2012 | McCombie et al. | 600/324 |
| 2013/0060167 | A1 * | 3/2013 | Dracup et al. | 600/595 |

OTHER PUBLICATIONS

EpDetect User Manual (www.epdetect.com/EpDetect_user_manual.pdf, 2009).*

* cited by examiner

*Primary Examiner* — John A Tweel, Jr.
(74) *Attorney, Agent, or Firm* — Fish & Richardson P.C.

(57) ABSTRACT

A convulsive seizure detection and notification device includes an acceleration module to measure acceleration of a body part of a user and generate acceleration measurement values, a storage to store a first threshold value and a second threshold value, and a data processor to compare acceleration measurement data with the first and second threshold values and generate a signal if a predetermined relationship between the acceleration measurement data and the first and second threshold values is satisfied.

38 Claims, 5 Drawing Sheets

CONVULSIVE SEIZURE DETECTION AND NOTIFICATION SYSTEM

TECHNICAL FIELD

The present disclosure relates generally to convulsive seizure detection and notification systems.

BACKGROUND

Epilepsy is a neurological condition that is characterized by seizures. A seizure occurs when a group of neurons within the brain malfunction and fire simultaneously producing an excessive amount of neurological activity. There are many types of seizures, such as tonic, clonic, and tonic-clonic seizures. Tonic seizures are characterized by general muscle rigidity. Clonic seizures are characterized by repetitive involuntary muscle contractions that may appear as severe jerking motions. Tonic-clonic seizures begin with a tonic phase. Often patients at this time fall and their muscles may enter a stage of extreme hyperextension. After the tonic phase, the patient enters a generalized clonic phase, causing most muscle groups to spasm and contract, giving the appearance of convulsions.

Convulsive seizures can cause serious physical injury. In many cases, a quick response to an epileptic attack can prevent fatality and injury. Many convulsive seizures result in apnea which, when prolonged, can cause brain damage and even death. Patients who are standing during the onset of a seizure may sustain injuries from a fall. The convulsive characteristics attributed to seizures often result in general bodily trauma in the form of broken bones, head trauma, and tongue-bite. In some cases, the extreme-hypertension that occurs during the tonic phase of a seizure can cause skeletal damage, such as spinal fracturing, and can result in paralysis. Recent animal models suggest that seizures of both convulsive and non-convulsive nature can cause permanent damage to the brain. The post-ictal (post seizure) phase of a seizure can also be dangerous for a seizure patient. After having epileptic attacks, patients can suffer from amnesia and general confusion. Patients who sustained injuries from their seizures are often unable to assist themselves due to their mental and/or physical states. Patients are capable of further injuring themselves by reckless behavior.

SUMMARY

In general, in one aspect, an apparatus includes an acceleration module to measure acceleration of a body part of a user and generate acceleration measurement values; a storage to store a first threshold value and a second threshold value; and a data processor to compare acceleration measurement data with the first and second threshold values and generate a signal if at least two oscillations are detected. Each oscillation includes a first acceleration in a first direction having an amplitude greater than the first threshold followed by a second acceleration in a second direction having an amplitude greater than the second threshold.

Implementations of the apparatus may include one or more of the following features. The signal can include a message indicating a likelihood of a seizure. The time interval between the first and second accelerations can be greater than a predetermined amount of time. The apparatus can include a user interface to allow a user to adjust the value of the predetermined amount of time. The apparatus can include a location sensor, and the signal can include location information provided by the location sensor. The location sensor can include a global positioning system (GPS) receiver. The first direction can be opposite to the second direction. The apparatus can include a user interface to allow a user to adjust the first and second threshold values. The data processor generates the signal only if at least n oscillations are detected, n being an integer configurable by a user. The apparatus can include a user interface to allow a user to configure the value of n. The apparatus can include an alarm that is activated by the data processor after detecting the at least two oscillations. After detecting the at least two oscillations, the data processor can wait for a predetermined amount of time before generating the signal. The apparatus can include a mechanism to allow a user to prevent the signal from being generated after the alarm is activated. The alarm can include a buzzer or vibrator alarm.

In general, in another aspect, a system includes an acceleration module to measure acceleration of a body part of a user and output acceleration measurement values, and a phone that communicates wirelessly with the acceleration module. The phone includes a storage to store a first threshold value and a second threshold value; and a data processor to compare the acceleration measurement values with the first and second threshold values and generate a message if at least two oscillations are detected. Each oscillation includes a first acceleration in a first direction having an amplitude greater than the first threshold followed by a second acceleration in a second direction having an amplitude greater than the second threshold.

Implementations of the apparatus may include one or more of the following features. The phone can include a location sensor, and the message can include location information provided by the location sensor. The phone can include an app that when executed causes the data processor to compare the acceleration measurement values with the first and second threshold values and generate the message if at least two oscillations are detected. The signal can include a message indicating a likelihood of a seizure.

In general, in another aspect, a seizure detection and notification system includes an acceleration module to measure acceleration of a body part of a user and generate acceleration measurement values; a storage to store a first threshold value and a second threshold value; and a data processor to compare acceleration measurement data with the first and second threshold values and generate a message indicating a likelihood of a seizure if a predetermined relationship between the acceleration measurement data and the first and second threshold values is satisfied.

Implementations of the system may include one or more of the following features. The predetermined relationship can indicate detection of at least two oscillations, each oscillation including a first acceleration in a first direction having an amplitude greater than the first threshold followed by a second acceleration in a second direction having an amplitude greater than the second threshold. The time interval between the first and second accelerations can be greater than a predetermined amount of time.

In general, in another aspect, a method includes measuring acceleration of a body part of a user and generating acceleration measurement values; comparing the acceleration measurement values with a first threshold value and a second threshold value; and generating a signal if at least two oscillations are detected in which each oscillation includes a first acceleration in a first direction having an amplitude greater than the first threshold followed by a second acceleration in a second direction having an amplitude greater than the second threshold.

Implementations of the method may include one or more of the following features. Generating a signal can include generating a message indicating a likelihood of a seizure. The time interval between the first and second accelerations can be greater than a predetermined amount of time. The method can include generating location information, and generating a signal can include generating a signal that includes the location information. Generating location information can include generating location information based on global positioning system (GPS) signals. The first direction can be opposite to the second direction. Generating a signal can include generating a signal only if at least n oscillations are detected, n being an integer configurable by a user. The method can include activating an alarm after detecting the at least two oscillations. The method can include, after detecting the at least two oscillations, waiting for a predetermined amount of time before generating the signal. The method can include providing a mechanism to enable a user to prevent the signal from being generated after the alarm is activated. Measuring acceleration of a body part can include measuring acceleration of a wrist or a waist.

In general, in another aspect, a method includes measuring acceleration of a body part using an accelerometer attached to the body part, and outputting acceleration measurement values; transmitting the acceleration measurement values wirelessly to a phone; at the phone, comparing measured acceleration data with a first threshold value and a second threshold value; and at the phone, generating a message if at least two oscillations are detected. Each oscillation includes a first acceleration in a first direction having an amplitude greater than the first threshold followed by a second acceleration in a second direction having an amplitude greater than the second threshold, the time interval between the first and second accelerations being greater than a predetermined amount of time.

Implementations of the method may include one or more of the following features. The method can include generating location information using a location sensor, in which generating a message can include generating a message that includes the location information. The method can include executing an app at the phone to cause the phone to compare the measured acceleration data and to generate the message if at least two oscillations are detected. The message can indicate a likelihood of a seizure.

In general, in another aspect, a method includes measuring acceleration of a body part of a user and generating acceleration measurement values; comparing the acceleration measurement values with a first threshold value and a second threshold value; and generating a message indicating a likelihood of a seizure if a predetermined relationship between the acceleration measurement data and the first and second threshold values is satisfied.

Implementations of the method may include one or more of the following features. The predetermined relationship can indicate detection of at least two oscillations, each oscillation including a first acceleration in a first direction having an amplitude greater than the first threshold followed by a second acceleration in a second direction having an amplitude greater than the second threshold.

In general, in another aspect, a computer-readable medium storing an app comprising instructions that when executed on a mobile device causes the mobile device to perform: receiving acceleration measurement values; and comparing the acceleration measurement values with first and second threshold values and generate a message if at least two oscillations are detected. Each oscillation includes a first acceleration in a first direction having an amplitude greater than the first threshold followed by a second acceleration in a second direction having an amplitude greater than the second threshold, the time interval between the first and second accelerations being greater than a predetermined amount of time.

Implementations of the method may include the following feature. The message can indicate a likelihood of a seizure.

DETAILED DESCRIPTION

Figure 1:
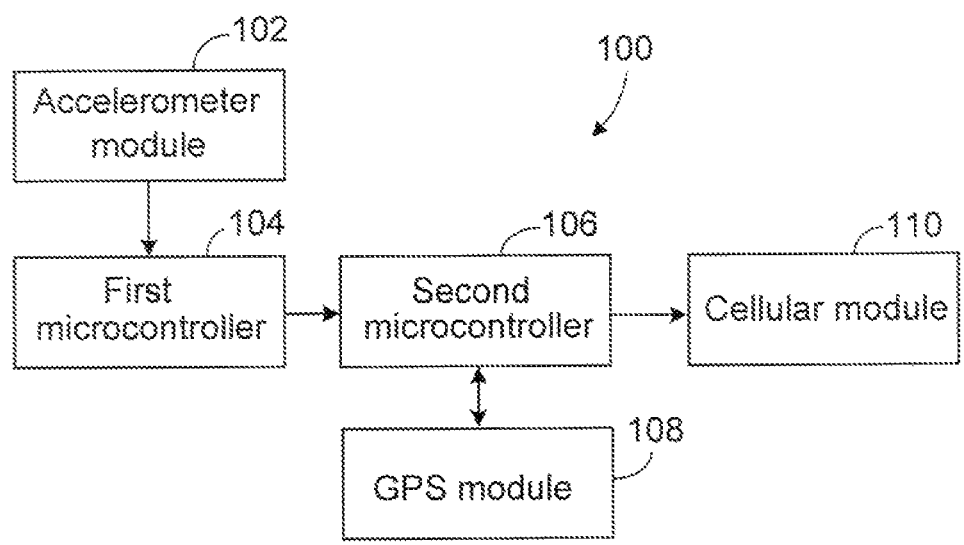
FIG. 1 is a block diagram of an example convulsive seizure detection and notification device.

Referring to FIG. 1, a convulsive seizure detection and notification device 100 includes an accelerometer module 102 that measures accelerations of a user's body part (e.g., waist or limb), and a first microcontroller 104 to process the measurements from the accelerometer module 102. Upon determining that the acceleration of the user's body part matches a typical seizure motion, the first microcontroller 104 triggers a second microcontroller 106 to obtain location information from a location sensor, such as a global positioning system (GPS) module 108. The second microcontroller 106 controls a cellular module 110 to send a series of customizable "request for help" text messages that may include the user's location and status information to designated persons, such as family members, friends, and emergency personnel. The text message can include important personal information such as medications used and doses taken. The device 100 is configurable so that it may be adapted to detect seizure characteristics of a wide variety of users. The device 100 can be configured and used by a patient with guidance from a physician or other qualified personnel.

In some implementations, the device 100 can be, e.g., attached to a belt or worn on a wrist.

In some implementations, the device 100 includes separate sub-modules that are worn on different parts of the user. For example, the device 100 may include a first sub-module and a second sub-module. The first sub-module may include the accelerometer module 102, and may be worn on the user's wrist. The second sub-module may include the first and second microcontrollers 104, 106, the GPS module 108, and the cellular module 110, and may be attached to the user's belt. The accelerometer module 102 may communicate with the first microcontroller 104 wirelessly, such as using a Bluetooth link. Measuring the acceleration motions of the user's wrist may allow more accurate detection of seizure than measuring the motions of the user's waist. By separating the accelerometer module 102 from the other modules, the module attached to the user's wrist can be made small, making it more comfortable to the user. There can be more than one accelerometer module. For example, two or more accelerometer modules can be worn on the user's wrists, ankles, and/or waist. Each accelerometer module may include two or more accelerometers that measure the acceleration in two or more directions, such as x, y, and z directions.

The first microcontroller 104 analyzes the acceleration data using a real-time threshold comparison algorithm to detect the characteristic clonic jerks associated with convulsive seizures. The algorithm is based on observations indicating that typical seizure motions are characterized by high amplitude contrasting acceleration spikes. The algorithm was verified using data obtained from analyses of videos of patients under seizure. Different people may show different behaviors during seizures. It is preferable to seek advice from a qualified medical professional when configuring the device 100 for use by a particular patient.

The threshold comparison algorithm is designed to differentiate motions that are typical of normal body movements from motions that indicate seizures. Typical hand motions such as reaching for a handshake or getting a drink may produce a slight vertical and horizontal acceleration of the hand. For example, a graph of the vertical acceleration of a person's wrist before, during, and after a handshake may show a small "bump" on the graph during the start of the handshake (indicating upward acceleration). In this scenario, there is little or no negative acceleration (downward acceleration). Other typical hand motions include reflexes. A graph of the acceleration of a reflex may include a spike of significantly larger amplitude than that made by the handshake. The graph may also indicate little or no negative acceleration. Generally, normal hand motions involve relatively slow accelerations, and often do not produce a positive acceleration immediately followed by a negative acceleration, or the reverse, which are referred to as contrasting acceleration spikes.

Convulsive seizures produce contrasting acceleration spikes of high amplitudes. The threshold comparison algorithm is based on the extremity of acceleration during a seizure, and the contrasting acceleration spikes that occur during the seizure. The device 100 detects seizures by periodically comparing measurement values provided by the accelerometer module 102 to preset thresholds. The thresholds are determined based on the typical acceleration of the user's body part when having a seizure. The thresholds are different depending on where the accelerometer module 102 is attached to the user. For example, if the accelerometer module 102 is attached to the user's belt, a first set of threshold values may be used, and if the accelerometer module 102 is worn on the user's wrist, a second set of threshold values may be used.

If an accelerometer monitoring the acceleration of a limb reports accelerations that exceed the thresholds repeatedly for a period of time, there is a high likelihood that the patient is having a seizure. The threshold comparison algorithm can be expressed as:

$$\left( \frac{\sum_{i=0}^{k-1} [a_{n+i(\Delta d)} \geq t_{top}] \& [a_{n+(\exists x \geq \Delta d)+i(\Delta d)} \leq t_{bot}]}{S_{min}} \right) \geq 1$$

The meanings of the variables are as follows:
k: the number of oscillations to test for;
$\{a_1, a_2, a_3, \ldots a_n\}$: the set of accelometry data;
$\Delta d$: the constant that represents the average number of accelometry inputs before the next change in direction;
$t_{top}$: the upper acceleration threshold;
$t_{bot}$: the lower acceleration threshold; and
$s_{min}$: the number of oscillations for a user to be assumed having a seizure.

When the value in the left hand side of the above formula is greater than or equal to one, there is a high likelihood that the user is having a seizure.

During a convulsive seizure, the user's limb may accelerate in a specific direction followed by a quick change in the direction of acceleration. For example, assume that the set $\{a_1, a_2, a_3, \ldots a_n\}$ represents the data returned from an accelerometer that measures the veritcal acceleration of the user's wrist. During a seizure, the user's wrist may accelerate upwards vertically for a short period of time, stop, then change direction and begin a vertical descent. During the upward movement, the acceleration of the user's wrist may be equal to or greater than the threshold $t_{top}$:

$$\therefore (\exists a_n \geq t_{top})$$

Similarly, during the downward movement, the acceleration of the user's wrist may be equal to or smaller than the threshold $t_{bot}$:

$$\therefore (\exists a_n \leq t_{bot})$$

The threshold $t_{bot}$ is a negative value. Here, a positive value for $a_n$ indicates an upward acceleration, and a negative value for $a_n$ indicates a downward acceleration.

The change in direction from an upward movement to a downward movement occurs after the first threshold $t_{top}$ is exceeded. Given that the accelerometer module 102 provides measurement values at regular intervals, the amount of time it takes to change the direction of acceleration can be expressed as some constant $\Delta d$.

$$\therefore (\exists a_{n+\Delta d} \leq t_{bot})$$

To detect a single oscillation of the user's wrist while ensuring that the accelerations surpass the upper and lower thresholds, the following algorithm can be used:

$$\therefore [a_n \geq t_{top}] \wedge [a_{n+(\exists \chi \geq \Delta d)} \leq t_{bot}]$$

If the above formula evaluates to 1, it indicates that the user's wrist has oscillated once and the accelerations exceeded the upper and lower thresholds. Detection of a single oscillation having accelerations exceeding the upper and lower thresholds may not be sufficient to accurately determine that the user is having a seizure. Thus, it is useful to look for an additional oscillation after the first oscillation using the following formula:

$$\therefore ([a_n \geq t_{top}] \wedge [a_{n+(\exists \chi \geq \Delta d)} \leq t_{bot}]) + ([a_{n+\Delta d} \geq t_{top}] \wedge [a_{n+(\exists \chi \geq \Delta d)+\Delta d} \leq t_{bot}])$$

Two oscillations may also not be sufficient to accurately determine that the user is having a seizure. Thus, a variable k is defined as the number of oscillations to check for.

$$\therefore \sum_{i=0}^{k-1} [a_{n+i(\Delta d)} \geq t_{top}] \wedge [a_{n+(\exists x \geq \Delta d)+(\Delta d)} \leq t_{bot}]$$

The above formula can be used to indicate the number of oscillations of the user's limb having accelerations that exceed the upper and lower thresholds. In order to check if the user is having a seizure, the number of oscillations detected is compared to a constant $s_{min}$ that represents the minimum number of oscillations one typically undergoes during a seizure.

$$\left( \frac{\sum_{i=0}^{k-1} [a_{n+i(\Delta d)} \geq t_{top}] \& [a_{n+(\exists x \geq \Delta d)+i(\Delta d)} \leq t_{bot}]}{S_{min}} \right) \geq 1$$

If the above formula is true, there is a high likelihood that the user is having a convulsive seizure.

Figure 2:
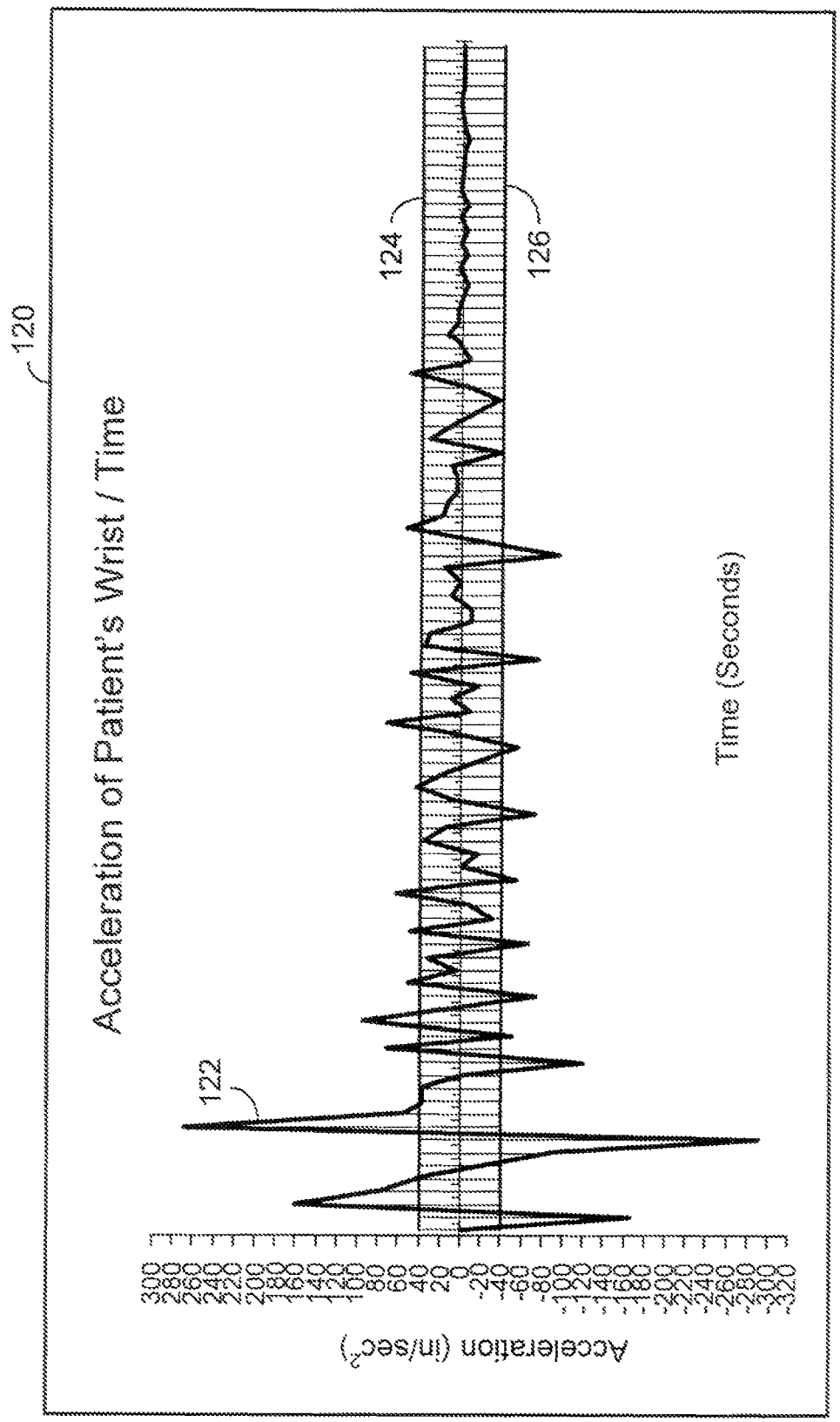
FIG. 2 is a graph showing example accelerations of a wrist of a patient having a seizure.

Referring to FIG. 2, a graph 120 shows a line 122 representing accelerations of the wrist of a patient having a seizure. The accelometry data were derived from a video of a patient having a convulsive seizure. The video was converted into a series of images at one frame per second. This may have reduced accuracy as some shaking may have occurred in between the frames. However, any convulsions between the frames may likely be of small magnitude and little importance. Using an image editing software, a magenta point was placed on the wrist of the patient in every image frame.

A program was written to track the movement of the magenta point from frame to frame. The program determined the velocity and acceleration of the patient's wrist. The values of the accelerations were scaled according to the size of the patient. The program provides a graphical user interface that shows a graph, such as the graph 120, to allow the user to easily determine appropriate thresholds for the seizure detection algorithm. Other methods for determining the threshold values can also be used.

In this example, an upper horizontal line 124 indicates the upper threshold, and a lower horizontal line 126 indicates the lower threshold. Here, the upper threshold is 40 inches/second$^2$, and the lower threshold is −40 inches/second$^2$. Other threshold values can also be used. The threshold values can be adjusted by the user.

The program can be executed on a personal computer or a smart phone, and the device 100 can communicate with the computer or smart phone, e.g., by using a USB (universal serial bus) connection. After the user selects the upper and lower thresholds, the user can configure the device 100 to store the upper and lower threshold values, and use the stored threshold values for detection of a seizure in the future.

Figure 3:
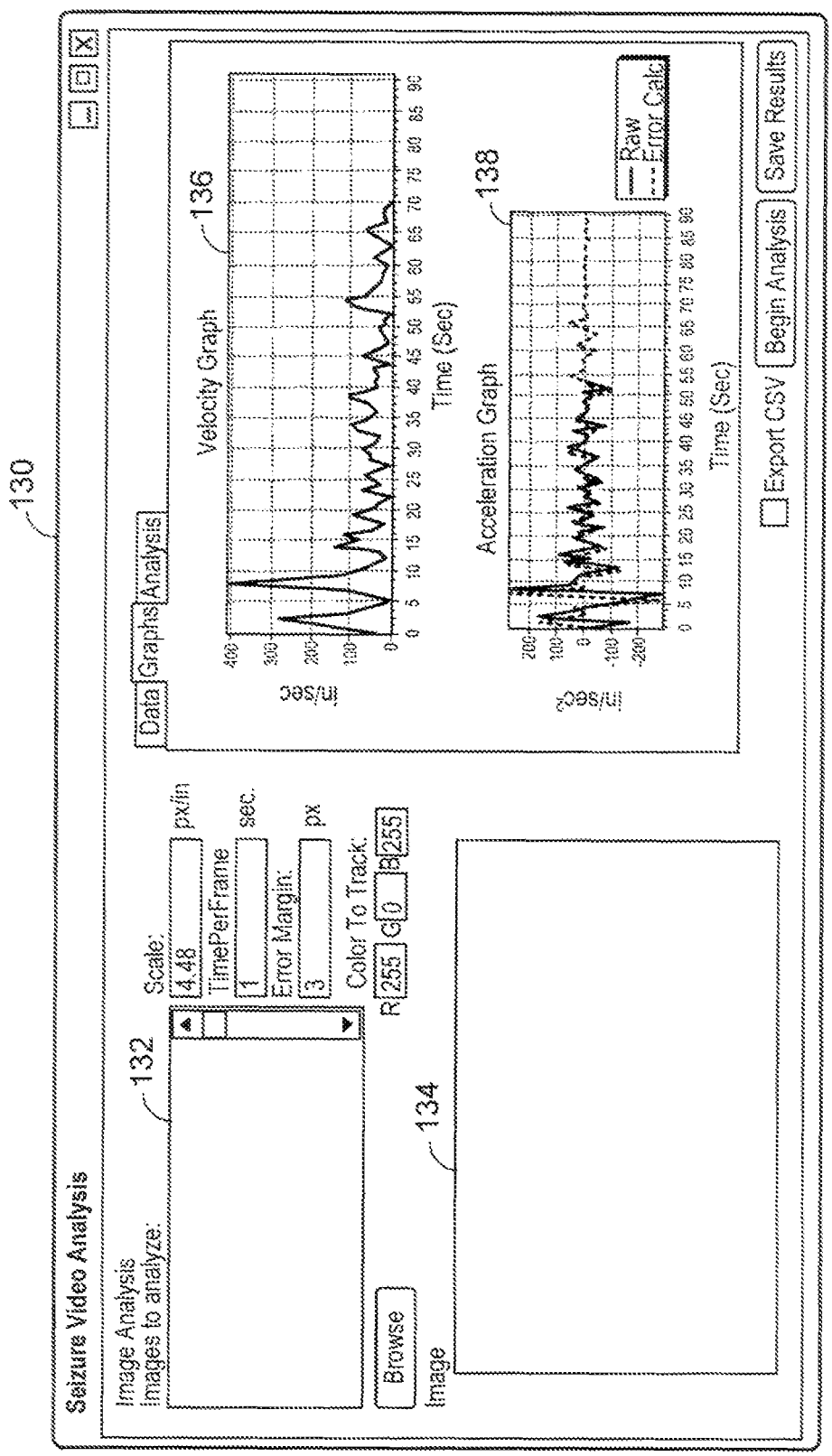
FIG. 3 is an example graphical user interface.

Referring to FIG. 3, a graphical user interface (GUI) 130 may be provided to allow a user to determine the upper and lower acceleration threshold values. The GUI 130 may include a window 132 showing images to analyze, and a window 134 showing a specific image. The images may be those of the user or another person having a seizure. For example, if the user had a past seizure that was captured in a video, the video may be analyzed for use in helping detect future seizures.

A velocity graph 136 may be shown to indicate the velocity of the movements of the user's body part. An acceleration graph 138 may be provided to show the accelerations of the movements of the user's body part. The acceleration graph 138 may show raw measurement data and data adjusted for errors (e.g., to compensate for errors in processing the images, such as the placement of the magenta points in the images). The GUI 130 may provide additional information and additional tools for analyzing the data.

Figure 4:
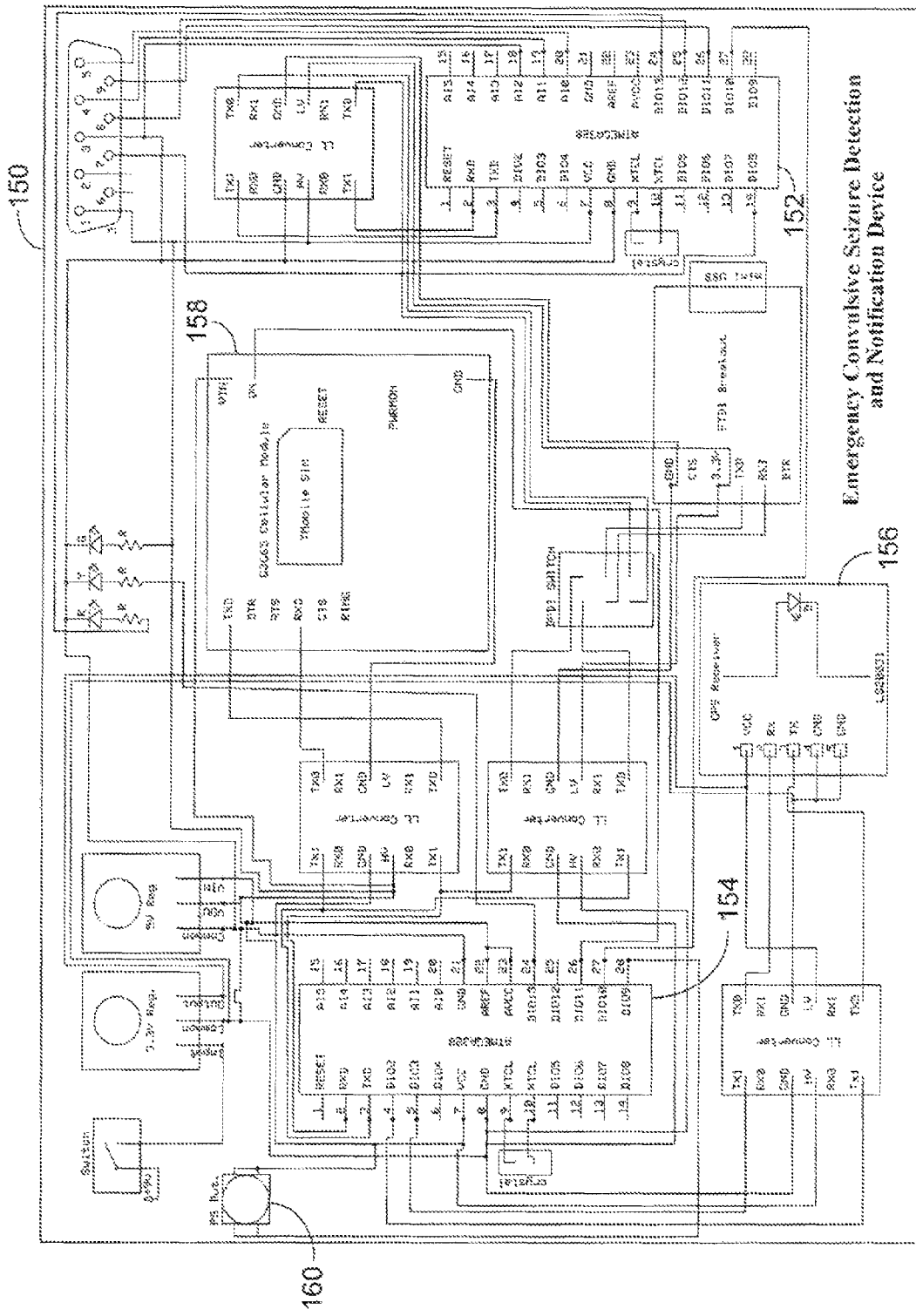
FIG. 4 is a schematic diagram of an example seizure detection and notification device.

Referring to FIG. 4, in some implementations, an emergency convulsive seizure detection and notification device 150 includes two atMega328 microcontrollers 152, 154 that perform the functions of the first and second microcontrollers 104, 106 in FIG. 1. The first microcontroller 152 is connected to an accelerometer and performs real-time seizure-detection processing. The second microcontroller 154 is responsible for communicating with a GPS receiver 156 and a cellular modem 158. When the first microcontroller 152 detects a convulsive seizure by using the seizure detection algorithm, a buzzer and a vibration motor are triggered. These alarms have two functions: to alert bystanders of the patient's status and to alert the patient in the case of a false alarm. If the patient is not having a seizure, the patient has the option of pressing a button 160 to cancel the alarm and prevent the device 150 from contacting friends, family, and emergency personnel. If the patient does not press the button before a preset amount of time, the patient is assumed to be having a seizure and the second microcontroller 154 is triggered. The second microcontroller 154 queries the GPS receiver 156 for the patient's coordinates and communicates with the cellular modem 158 to send a text message. The text message is sent to a list of predefined phone numbers, notifying the recipients of the patient's location and status.

A feature of the device 100 or 150 is that the device is configurable. The seizure detection thresholds can be manually set by the user to increase the device's detection accuracy. The text within the emergency message can be customized to include medications, doses taken, and other information that emergency personnel may find useful. The recipients of the emergency messages can be modified to include as many phone numbers as the memory of the device 100 or 150 permits.

The device 100 or 150 can be configured in a number of ways, such as by direct serial communication using a device custom command protocol, or using a custom configuration program. In both cases the device 100 or 150 is connected to a computer by, e.g., a USB cable, and then re-configured. The settings of the device (including the upper and lower thresholds) can be stored on EEPROM (electrically erasable programmable read only memory), flash memory, or other types of non-volatile memory so that the settings are maintained after the device powers down.

Figure 5:
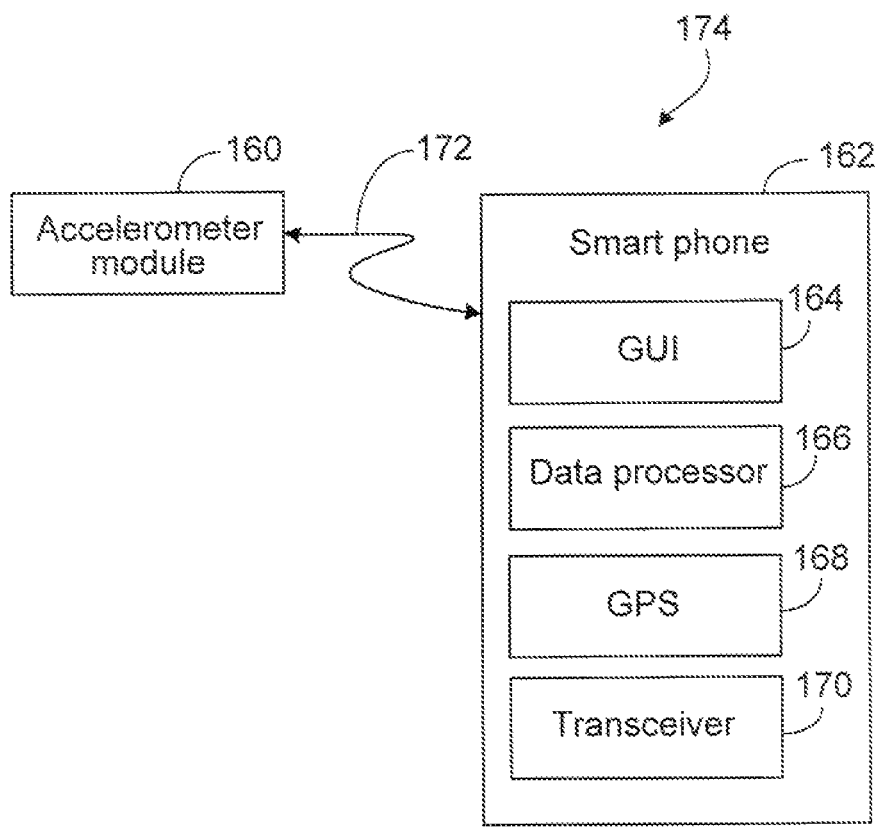
FIG. 5 is a block diagram of an example convulsive seizure detection and notification device that uses a smart phone.

Referring to FIG. 5, in some implementations, a seizure detection and notification system 174 includes an accelerometer module 160 and a smart phone 162 executing a seizure detection and notification program. The accelerometer module 160 communicates through a wireless link 172 with the smart phone 162, which analyzes measurement data from the accelerometer module 160 to detect seizure. The wireless link 172 can be, e.g., a Bluetooth link. At the smart phone 162, a graphical user interface 164 is provided to allow the user to configure the upper and lower acceleration thresholds, and to edit text messages to be sent to emergency contact persons in the event of a seizure. A data processor 166 analyzes the acceleration measurements, and a GPS unit 168 provides location information. A transceiver 170 enables the smart phone 162 to communicate with a wireless base station for sending text messages. In some implementations, the seizure detection and notification program can be downloaded as an app and installed on the smart phone 162. The seizure detection and notification program can implement the threshold comparison algorithm described above to analyze the acceleration data to detect seizure.

The smart phone 162 can either be worn by the user or be placed at a location near the user such that the accelerometer module 160 can communicate with the smart phone 162. The smart phone 162 may generate an alarm signal when the accelerometer module 160 is out of range so that the user can move the smart phone 162 to a location closer to the user.

The smart phone 162 may be replaced by other mobile devices, such as a tablet computer or a notebook computer. The accelerometer module 160 may be powered by battery, the movements of the user (e.g., by using a device that harvests kinetic energy), or a combination of the above.

In some implementations, the accelerometer module 160 communicates with processing modules that are capable of processing the acceleration measurement data, in which the modules are not necessarily mobile devices. For example, if the user stays in a house, each room in the house may have a processing module that can receive and process the acceleration measurement data from the accelerometer module 160 and send an alert message in the event of a seizure. As the user moves from room to room in the house, the accelerometer module 160 establishes links with the processing module in the room so that at any given time, at least one processing module is receiving and processing the acceleration measurement data from the accelerometer module 160.

A number of implementations have been described. Nevertheless, it will be understood that various modifications may be made. For example, elements of one or more implementations may be combined, deleted, modified, or supplemented to form further implementations. As yet another example, the logic flows depicted in the figures do not require the particular order shown, or sequential order, to achieve desirable results. In addition, other steps may be provided, or steps may be eliminated, from the described flows, and other components may be added to, or removed from, the described systems.

For example, the first and second microcontrollers 104, 106 can be combined in one microcontroller. Microcontrollers other than the atMega328 microcontrollers can be used. Instead of a GPS module, other modules that provide location information can be used, such as modules based on cell tower triangulation or WiFi triangulation. Instead of a cellular module, other communication modules can be used. For example, the device 100 can wirelessly communicate with a smart phone in the event that a seizure is detected, and the smart phone may be configured to send emergency alert messages.

In the example above, the upper threshold is a positive value and the lower threshold is a negative value. An acceleration in a first direction is represented as a positive value, and an acceleration in an opposite direction is represented as a negative value. This is useful for detecting accelerations along a linear direction, such as along a vertical direction. In some examples, a first threshold and a second threshold that are both positive values can be used. The amplitude of the acceleration in a first direction is compared with the first threshold, and the amplitude of the acceleration in a second direction is compared with the second threshold. The first and second thresholds can have the same or different values. The first and second directions can be opposite to each other, or at any angle between about 90° to 270° relative to each other. The directions of accelerations may vary in three-dimensional space over time. For example, a patient's limb may initially have up/down jerking motions, then later have left/right jerking motions as the body position changes. Each of the first and second microcontrollers 104, 106 can be a data processor, such as a microprocessor unit. The smart phone 162 in FIG. 5 can be replaced by another mobile device that can perform the functions of comparing acceleration measurement data with threshold values, and generating an alert message in the event that the comparison indicates a likelihood of an occurrence of a seizure. The threshold comparison algorithm can be modified to detect particular movement patterns of particular patients, in which the particular movement patterns can be determined based on past seizures of the patients.

Accordingly, other implementations are within the scope of the following claims.

What is claimed is:

1. An apparatus comprising:
    an acceleration module to measure acceleration of a body part of a user and generate acceleration measurement values;
    a storage to store a first threshold value and a second threshold value; and
    a data processor to compare acceleration measurement data with the first and second threshold values and generate a signal if at least two oscillations are detected in which each oscillation includes a first acceleration in a first direction having an amplitude greater than the first threshold followed by a second acceleration in a second direction having an amplitude greater than the second threshold.

2. The apparatus of claim 1 in which the signal comprises a message indicating a likelihood of a seizure.

3. The apparatus of claim 1 in which the data processor generates the message indicating a likelihood of a seizure upon detecting oscillations occurring repeatedly for a time interval greater than a predetermined amount of time.

4. The apparatus of claim 3, comprising a user interface to allow a user to adjust the value of the predetermined amount of time.

5. The apparatus of claim 1, comprising a location sensor, and the signal includes location information provided by the location sensor.

6. The apparatus of claim 5 in which the location sensor comprises a global positioning system (GPS) receiver.

7. The apparatus of claim 1 in which the first direction is opposite to the second direction.

8. The apparatus of claim 1, comprising a user interface to allow a user to adjust the first and second threshold values.

9. The apparatus of claim 1 in which the data processor generates the signal only if at least n oscillations are detected, n being an integer configurable by a user.

10. The apparatus of claim 9, comprising a user interface to allow a user to configure the value of n.

11. The apparatus of claim 1, comprising an alarm that is activated by the data processor after detecting the at least two oscillations.

12. The apparatus of claim 11 in which after detecting the at least two oscillations, the data processor waits for a predetermined amount of time before generating the signal.

13. The apparatus of claim 12 comprising a mechanism to allow a user to prevent the signal from being generated after the alarm is activated.

14. The apparatus of claim 11 in which the alarm comprises at least one of a buzzer or vibrator alarm.

15. A system comprising:
    an acceleration module to measure acceleration of a body part of a user and output acceleration measurement values; and
    a phone that communicates wirelessly with the acceleration module, the phone comprising
    a storage to store a first threshold value and a second threshold value; and
    a data processor to compare the acceleration measurement values with the first and second threshold values and generate a message if at least two oscillations are detected in which each oscillation includes a first acceleration in a first direction having an amplitude greater than the first threshold followed by a second acceleration in a second direction having an amplitude greater than the second threshold.

16. The system of claim 15 in which the phone comprises a location sensor, and the message includes location information provided by the location sensor.

17. The system of claim 15 in which the phone comprises an app that when executed causes the data processor to compare the acceleration measurement values with the first and second threshold values and generate the message if at least two oscillations are detected.

18. The system of claim 15 in which the signal comprises a message indicating a likelihood of a seizure.

19. An apparatus comprising:
    an acceleration module to measure acceleration of a body part of a user and generate acceleration measurement values;

a storage to store a first threshold value and a second threshold value; and a data processor to compare acceleration measurement data with the first and second threshold values and generate a message indicating a likelihood of a seizure if a predetermined relationship between the acceleration measurement data and the first and second threshold values is satisfied, in which the predetermined relationship indicates detection of at least two oscillations, each oscillation including a first acceleration in a first direction having an amplitude greater than the first threshold followed by a second acceleration in a second direction having an amplitude greater than the second threshold.

20. The apparatus of claim 19 in which the data processor generates the message indicating a likelihood of a seizure upon detecting oscillations occurring repeatedly for a time interval greater than a predetermined amount of time.

21. A method comprising:

measuring acceleration of a body part of a user and generating acceleration measurement values;

comparing the acceleration measurement values with a first threshold value and a second threshold value; and generating a signal if at least two oscillations are detected in which each oscillation includes a first acceleration in a first direction having an amplitude greater than the first threshold followed by a second acceleration in a second direction having an amplitude greater than the second threshold.

22. The method of claim 21 in which generating a signal comprises generating a message indicating a likelihood of a seizure.

23. The method of claim 21 in which the data processor generates the message indicating a likelihood of a seizure upon detecting oscillations occurring repeatedly for a time interval greater than a predetermined amount of time.

24. The method of claim 21, comprising generating location information, and generating a signal comprises generating a signal that includes the location information.

25. The method of claim 24 in which generating location information comprises generating location information based on global positioning system (GPS) signals.

26. The method of claim 21 in which the first direction is opposite to the second direction.

27. The method of claim 21 in which generating a signal comprises generating a signal only if at least n oscillations are detected, n being an integer configurable by a user.

28. The method of claim 21, comprising activating an alarm after detecting the at least two oscillations.

29. The method of claim 28, comprising, after detecting the at least two oscillations, waiting for a predetermined amount of time before generating the signal.

30. The method of claim 29, comprising providing a mechanism to enable a user to prevent the signal from being generated after the alarm is activated.

31. The method of claim 21 in which measuring acceleration of a body part comprises measuring acceleration of at least one of a wrist or a waist.

32. A method comprising:

measure acceleration of a body part using an accelerometer attached to the body part, and outputting acceleration measurement values;

transmitting the acceleration measurement values wirelessly to a phone;

at the phone, comparing measured acceleration data with a first threshold value and a second threshold value; and at the phone, generating a message if at least two oscillations are detected in which each oscillation includes a first acceleration in a first direction having an amplitude greater than the first threshold followed by a second acceleration in a second direction having an amplitude greater than the second threshold, the time interval between the first and second accelerations being greater than a predetermined amount of time.

33. The method of claim 32, comprising generating location information using a location sensor, wherein generating a message comprises generating a message that includes the location information.

34. The method of claim 32, comprising executing an app at the phone to cause the phone to compare the measured acceleration data and to generate the message if at least two oscillations are detected.

35. The method of claim 32 in which the message indicates a likelihood of a seizure.

36. A method comprising:

measuring acceleration of a body part of a user and generating acceleration measurement values;

comparing the acceleration measurement values with a first threshold value and a second threshold value; and generating a message indicating a likelihood of a seizure if a predetermined relationship between the acceleration measurement data and the first and second threshold values is satisfied, in which the predetermined relationship indicates detection of at least two oscillations, each oscillation including a first acceleration in a first direction having an amplitude greater than the first threshold followed by a second acceleration in a second direction having an amplitude greater than the second threshold.

37. A computer-readable medium storing an app comprising instructions that when executed on a mobile device causes the mobile device to perform:

receiving acceleration measurement values; and comparing the acceleration measurement values with first and second threshold values and generate a message if at least two oscillations are detected in which each oscillation includes a first acceleration in a first direction having an amplitude greater than the first threshold followed by a second acceleration in a second direction having an amplitude greater than the second threshold, the oscillations occurring repeatedly for a time interval greater than a predetermined amount of time.

38. The computer-readable medium of claim 37 in which the message indicates a likelihood of a seizure.

\* \* \* \* \*